US005928909A

United States Patent [19]
Prakash et al.

[11] Patent Number: 5,928,909
[45] Date of Patent: Jul. 27, 1999

[54] REGIOSELECTIVE α-HYDROLYSIS OF AMINO ACID DIESTERS USING PIG LIVER ESTERASE

[75] Inventors: Indra Prakash; David J. Ager, both of Hoffman Estates; David P. Pantaleone, Buffalo Grove, all of Ill.

[73] Assignee: NSC Technologies LLC, Mount Prospect, Ill.

[21] Appl. No.: 09/013,032

[22] Filed: Jan. 26, 1998

Related U.S. Application Data

[62] Division of application No. 08/703,372, Aug. 26, 1996, Pat. No. 5,773,261.

[51] Int. Cl.$^6$ ............................. C12P 13/04; C12P 13/14; C12P 13/20
[52] U.S. Cl. ......................... 435/106; 435/109; 435/110; 435/197
[58] Field of Search .................................. 435/106, 109, 435/110, 197

[56] References Cited

FOREIGN PATENT DOCUMENTS 226014   8/1995   German Dem. Rep. .
52-128321 10/1977   Japan .

OTHER PUBLICATIONS

Wieczorek, W. et al., "α–Hydroxymethylaspartic acid: Synthesis and absolute configuration by X–ray analysis of its derivative (+)–4 benzoylamino–4–carboxy–γ–butyrolactone," J. Crystallogr. Spectrosc. Res., 1991, 21, 107.

Liu, K.–C. et al., "Synthesis of N–Substituted β–Methyl DL–Aspartates as Potential Hypocholesteremics," Arch. Pharmaz., 1975, 308, 564.

Bodanszky, M., "Principals of Peptide Synthesis," (Springer–Verlag), 1984, 84–89.

Bodanszky, M. et al., "The Practice of Peptide Synthesis" (Springer–Verlag), 1984, 12, 13 and 20.

Ohfune, Y. et al., "An Efficient One–Step Reductive N–Monoalkylation of α–Amino Acids," Chem. Letters, 1984, 441.

Stein, Karin A., et al., "Enzyme catalyzed regioselective hydrolysis of aspartate diesters," Chemical Abstracts, vol. 1996, Abstract No. 220614, Columbus, Ohio, US.

Prakash, Indra et al., "Pig liver esterase catalyzed regio– and chemoselective hydrolysis of amino acid diesters," Chemical Abstracts, vol. 1996, Abstract No. 415167, Columbus, Ohio, US.

Ohno, M. and Otsuka, M., "Chiral Synthons By Ester Hydrolysis Catalyzed By Pig Liver Esterase," Organic Reactions, 1989, vol. 37, Chapter 1.

Hultin, P.G. et al., "Enzymes in Organic Synthesis. 48. Pig Liver Esterase and Porcine Pancreatic Lipase Catalyzed Hydrolyses of 3,4–(Isopropylidenedioxy)–2,5–tetrahydrofuranyl Diesters," J. Org. Chem., 1991, 56, 5375.

Kobayashi S. et al., "The First Enantioselective Synthesis of Fortamine, the 1,4–Diaminocyclitol Moiety of Fortimicin A, by Chemicoenzymatic Approach," J. Org. Chem., 1990, 55, 1169.

Adachi, K. et al., "Chiral Synthons by Enantioselective Hydrolysis of meso–Diesters with Pig Liver Esterase: Substrate–Stereoselectivity Relationships," Chima, 1986, 40, 311.

Stein, K.A. et al., "Enzyme–Catalyzed Regioselective Hydrolysis of Asparate Diesters," J. Org. Chem., 1995, 60, 8110.

Albert, R. et al., "A Simple and Convenient Synthesis of β–Aspartates and γ– Glutamates," Synthesis, 1987, 635.

Metz, P., "Preparation of Enantiomerically Pure 3–Endo–Sulfonylmethyl Substituted Bicyclo [2.2.1] Heptane–2–Endo–Carboxylic Acids," Tetrahedron, 1989, vol. 45, 1989, 7311.

Van der Eycken, J., et al., "Enzymatic Preparation of Optically Active Bicyclo[2.2.1]heptene Derivatives, Building Blocks for Terpenoid Natural Products. An Attractive Alternative to Enantioselective Diels–Alder Syntheses," J. Chem. Soc., Chem. Commun., 1989, 306.

Sabbioni, G. et al., "Enzymes in Organic Synthesis. 39. Preparation of Chiral Cyclic Acid–Esters and Bicyclic Lactones via Stereoselective Pig Liver Esterase Catalyzed Hydrolyses of Cyclic Meso Diesters," J. Org. Chem. 52, 1987, 4565.

Sabbioni, G. et al., "Preparations of Bicyclic Chiral Lactone Synthons via Stereospecific Pig Liver Esterasecatalysed Hydrolyses of meso–Diesters. Ring–size induced Reversal of Stereospecificity," J. Chem. Soc., Chem. Commun., 1984, 236.

Jongejan, J.A. and Duine, J.A., "Enzymatic Hydrolysis of Cyclopropyl Acetate, A Facile Method for Medium– and Large–Scale Preparations of Cyclopropanol," Tetrahedron Lett., 1987, 28, 2767.

Hazato, A. et al., "Hydrolysis of Prostaglandin $E_1$ Methyl Ester and Analogues with Pig Liver Esterase," Nippon Kagaku Kaishi 1983, 9, 1390; Chem. Abstr.,1984, 100, 120720q.

Swann, Jr. S. et al., "Ethyl Hydrogen Sebacate," Org. Syntheses Coll. vol. II, 1943, 276.

March, J., Advanced Organic Chemistry, Third Ed. 1985, 347.

Durham, L.J. et al., J., "Methyl Hydrogen Hendecanedioate," Org. Syntheses Coll. vol. IV, 1963, 635.

(List continued on next page.)

*Primary Examiner*—Herbert J. Lilling
*Attorney, Agent, or Firm*—Fitzpatrick, Cella, Harper & Scinto

[57] ABSTRACT

The regioselective and chemoselective hydrolysis of an α-ester group of an amino acid diester using pig liver esterase enzyme (PLE) is disclosed. The amino acid diesters may be either N-protected or unprotected and the diester groups may be the same or different. In particular, the preparation of a number of γ-ester glutamates and β-ester aspartates are provided.

14 Claims, No Drawings

OTHER PUBLICATIONS

Prestidge, R.L. et al., "A Novel High–Yield Synthesis of γ Esters of Glutamic Acid and β Esters of Aspartic Acid by the Coppert–Catalyzed Hydrolysis of Their Diesters," J. Org. Chem., 1975, 40, 3287.

Guibe–Jampel, E. et al., "Enantioselective Hydrolysis of Racemic Diesters by Porcine Pancreatic Lipase," J. Chem. Soc., Chem. Commun., 1987, 1080.

Miyazawa, T. et al., "Optical Resolution of Unusual Amino–Acids by Lipase–catalysed Hydrolysis," J. Chem. Soc., Chem. Commun., 1988, 1214.

Cohen, S.G. et al., "Action of α–Chymotrypsin on Diethyl N–Acetyl–aspartate," Biochemistry, 1963, 2, 820.

Cohen, S.G. et al., "Kinetics of Hydrolysis of Dicarboxylic Esters and Their α–Acetamido Derivatives by α–Chymotrypsin," J. Am. Chem. Soc., 1964, 86, 4999.

Chung–gi Shin, et al., "Dehydrooligopeptides. XIII. Selective Enzymatic Hydrolysis of N–Protected α–Dehydroglutamic Acid Diesters and Their Analogs Using Papain as Catalyst," Bulletin Chemical Society of Japan, vol. 64, No. 12, 1991, pp. 3575–3580.

Chen, S.T. et al., "The Synthesis of β–Benzyl L–Aspartate and γ–Benzyl L–Glutamate by Enzyme–Catalyzed Hydrolysis," J. of Synth. Organic Chem., Synthesis, 1987, 581.

Pugniere, M. et al., "Enzymatic Synthesis of Side Chain Benzyl Esters of L–α–Amino Dicarboxylic Acids,", Tetrahedron: Asymmetry, 1992, 3, 1015.

Roeske, R., J., "Preparation of t–Butyl Esters of Free Amino Acids," J. of Org.Chem. 28, 1963, 1251.

Oki, K. et al., "The Resolution of N–Benzyloxylcarbonyl–DL–amino Acids Using Ephedrine," Bull. Chem. of the Society of Japan, 43, 1969, 2554.

Marchatti, E., Ann. Chim., 1967, 57. 624.

REGIOSELECTIVE α-HYDROLYSIS OF AMINO ACID DIESTERS USING PIG LIVER ESTERASE

This application is a divisional of application Ser. No. 08/703,372 filed Aug. 26, 1996 now U.S. Pat. No. 5,773,261.

BACKGROUND OF THE INVENTION

1. Field of the Invention

The present invention relates to regioselective and chemoselective hydrolysis of an α-ester group, of an amino acid diester using pig liver esterase enzyme (PLE). The amino acid diesters may be N-protected or unprotected and the ester groups may be the same or different.

2. Related Background Art

Throughout this application various publications are referenced by arabic numerals within parentheses (e.g., "Ref. 2"). Full citations for these references may be found at the end of the specification immediately preceding the claims. Disclosures of these publications in their entireties are hereby incorporated by reference into this application to more fully describe the state of the art to which this invention pertains.

PLE has been used as a catalyst for the synthesis of chiral molecules via enantioselective ester hydrolysis (Ref. 1). PLE has also been used to catalyze the hydrolysis of cyclic meso diesters to prepare chiral half-esters (Ref. 2). Other uses of PLE have included the hydrolysis of ester groups of labile molecules in the synthesis of achiral molecules (Ref. 3).

Generally, acid-esters or half-esters may be prepared by any of the following methods: the esterification or transesterification of diacids with an alcohol in the presence of an acid catalyst (Refs. 5, 8a and 8b ); the hydrolysis of a cyclic anhydride with an alcohol (Refs. 6); or the hydrolysis of a diester with barium hydroxide (Ref. 7 and 9). It is often difficult to obtain a pure product (i.e. the monoester), using these methods due to the formation of a mixture of products formed during inefficient isolation procedures. The mixture of products may include the monoester, the diester, and the diacid. Additionally, these methods have the disadvantage of tending to give low yields of the monoester product.

The prior art reports several attempts to prepare amino acid monoesters by the selective hydrolysis of amino acid diesters Refs 4 and 11. Stein et al. demonstrated that the hydrolysis of aspartate dimethyl ester using PLE resulted in the hydrolysis of both ester groups, i.e. the α-ester group and the β-ester group (Ref. 4). The selectivity of the α-ester hydrolysis to the β-ester hydrolysis was found to be 98:2 for the formation of the corresponding aspartate monoesters In contrast, both the (R)-aspartate diethyl ester and (S)-aspartate diallyl ester are converted to their respective β-monoesters with PLE with complete regioselectivity hydrolysis of the α-ester group. In addition, it was found that the preferential hydrolysis for the α-ester position is found to be partially reversed when the aspartate is N-protected as its formamide. The selectivity for the N-protected aspartate was found to be 55:45 for the α-ester hydrolysis to the β-ester hydrolysis.

PLE has also been used by Adachi et al. in studying the regioselective hydrolysis of optically active unsymmetric diesters (Ref. 2h). In particular, Adachi et al. disclosed that the hydrolysis of dimethyl aspartate and dimethyl glutamate using crude PLE resulted in formation of a mixture of products due to hydrolysis of both ester groups. The hydrolysis of N-protected aspartates and N-protected glutamates using PLE also resulted in the formation of a mixture of products. Adachi et al. also reported that for the N-protected amino acid diesters hydrolysis was slower at the α-ester group than the β- or γ-ester groups. The faster hydrolysis of the N-protected aspartates and glutamates at the β- and γ-ester groups is believed to be due to the less crowded methyl ester group at these positions being preferably accommodated at the active site.

In addition to PLE other enzymes such as porcine pancreatic lipase (PPL) has been used for the regioselective hydrolysis of dialkyl amino acid esters (Ref. 10). Hydrolysis of N-protected dialkyl aspartates using PPL resulted in the regioselective hydrolysis of the β-ester group and formation of the corresponding N-protected α-ester aspartate. However, in the case of unprotected dimethyl aspartate and glutamate esters, selective hydrolysis with PPL was not observed.

Accordingly, the development of an effective method for the regioselective hydrolysis of both u-protected and unprotected amino acid diesters remains a challenging problem.

SUMMARY OF THE INVENTION

The present invention relates to the regioselective and chemoselective hydrolysis of an α-ester group of an amino acid diester using pig liver esterase enzyme (PLE). The amino acid diesters may be N-protected or unprotected and the diester group may be the same or different. In particular, the invention relates to a method for the preparation of γ-ester glutamate which comprises reacting a diester glutamate comprising an α-ester group and a γ-ester group with an amount of a pig liver esterase enzyme effective to hydrolyze selectively the α-ester group and form the γ-ester glutamate.

Furthermore, this invention relates to a method for the preparation of an N-protected β-ester aspartate which comprises reacting an N-protected diester aspartate comprising an α-ester group and a β-ester group with an amount of a pig liver esterase enzyme effective to hydrolyze selectively the α-ester group and form the N-protected β-ester aspartate.

Additionally, the invention provides for a method for the preparation of a β-ester aspartate or a γ-ester glutamate which comprises reacting the corresponding mixed diester aspartate or glutamate with PLE.

DETAILED DESCRIPTION OF THE INVENTION

The present invention relates to the regioselective and chemoselective hydrolysis of an α-ester group of an amino acid diester using pig liver esterase enzyme (PLE). The amino acid diesters may be N-protected or unprotected and the diester group may be the same or different. In particular, a method for the preparation of a γ-ester glutamate which comprises reacting a diester glutamate comprising an α-ester group and a γ-ester group with an amount of a pig liver esterase enzyme effective to hydrolyze selectively the α-ester group and form the γ-ester glutamate.

The invention provides for the method where the α-ester group and the γ-ester group of the γ-ester glutamate may be the same or different. Each of the α-ester group and the γ-ester group is an alkyl ester. In preferred embodiments, the α-ester group and the γ-ester group are independently selected from the group consisting of $CH_3OCO-$, $C_2H_5OCO-$, $(CH_3)_3COCO-$ and $C_6H_5CH_2OCO-$.

In one embodiment of the invention, the diester glutamate has an N-protecting group. The invention provides for the method where the α-ester group and the γ-ester group of the N-protected γ-ester glutamate may be the same or different. Each of the α-ester group and the γ-ester group is an alkyl ester. In preferred embodiments, the α-ester group and the γ-ester group are independently selected from the group consisting of CH₃OCO—, C₂H₅OCO—, (CH₃)₃COCO— and C₆H₅CH₂OCO—.

The invention also relates to a method for the preparation of an N-protected β-ester aspartate which comprises reacting an N-protected diester aspartate comprising an α-ester group and a β-ester group with an amount of a pig liver esterase enzyme effective to hydrolyze selectively the α-ester group and form the N-protected β-ester aspartate. The α-ester group and the β-ester group may be the same or different. Each of the α-ester group and the β-ester group is an alkyl ester. In preferred embodiments of the method the α-ester group and the β-ester group are independently selected from the group consisting of CH₃OCO—, C₂H₅OCO—, (CH₃)₃COCO— and C₆H₅CH₂OCO—.

The N-protecting groups for the methods described herein are selected from the group consisting of alkyl or alkyl carbonyl. Preferred examples of N-protecting groups are selected from the group consisting of CH₃CH₂—, CH₃CO—, C₆H₅CH₂CO—, C₆H₅CH₂OCO—, CH₃CH₂CO— and (CH₃)₃COCO—.

The invention further relates to a method for the preparation of a β-ester aspartate which comprises reacting a diester aspartate comprising an α-ester group and a β-ester group which are different with an amount of a pig liver esterase enzyme effective to hydrolyze selectively the α-ester group and form the β-ester aspartate. Each of the α-ester group and the β-ester group is an alkyl ester. In preferred embodiments of the method the α-ester group and the β-ester group are independently selected from the group consisting of CH₃OCO—, C₂H₅OCO—, (CH₃)₃COCO— and C₆H₅CH₂OCO—.

In the methods of the present invention the amount of pig liver esterase enzyme effective to hydrolyze selectively the α-ester group is preferably about 150 units to about 575 units, more preferably about 300 units to about 400 units, and most preferably about 300 units.

All of the methods described herein may be performed in the presence of a suitable buffer. The buffer is selected from the group consisting of phosphate, imidazole, piperazine-N, N'-bis(2-ethanesulfonic acid) (PIPES), N-2-acetamidoiminodiacetic acid (ACES) and 3-(N-morpholino) propanesulfonic acid (MOPS). In one preferred embodiment, the phosphate buffer is potassium. The presence of a buffer ensures that the pH of the reaction medium is constant:. The α-ester hydrolysis reaction is carried out preferably at a pH range of about 6 to about 8, and more preferably at a pH range of about 6.5 to about 7.5. Organic solvents can be also be added to the buffer to aid in substrate solubility. Examples of suitable solvents include acetone, methanol, ethanol, N,N'-dimethylformamide (DMF), tetrahydrofuran (THF) and the like.

The hydrolysis of N-protected dialkyl esters of aspartic acid using PLE results in 100% regioselective hydrolysis of the α-ester group and formation of the β-ester product, as illustrated in the following Scheme 1:

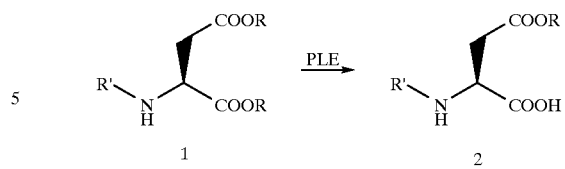

wherein R and R' are defined in Table 1.

Scheme 1. Reaction of N-protected aspartic acid diesters (Compound 1) with PLE.

Similarly, hydrolysis of N-protected and unprotected dialkyl esters of glutamic acid using PLE results in 100% regioselective hydrolysis of the α-ester group and formation of γ-alkyl esters, as illustrated in Scheme 2 below:

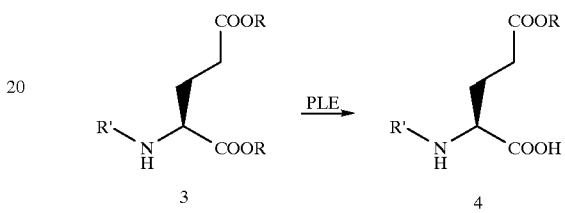

wherein R and R' are defined in Table 1.

Scheme 2. Reaction of N-protected and unprotected glutamic acid diesters (Compound 3) with PLE.

The rate of hydrolysis is faster when the amino acid diester substrate is soluble in the reaction medium and the enzyme is immobilized. When the amino acid diester substrate is present as a suspension, PLE also regioselectively hydrolyses the α-ester group.

In the case of mixed diester amino acid substrates, PLE regioselectively hydrolyses the α-ester position. Hydrolysis of N-protected and unprotected α-methyl β-t-butyl aspartate (5) and α-methyl γ-t-butyl ester glutamate (7) gives the corresponding α-acids, as illustrated in Scheme 3 below:

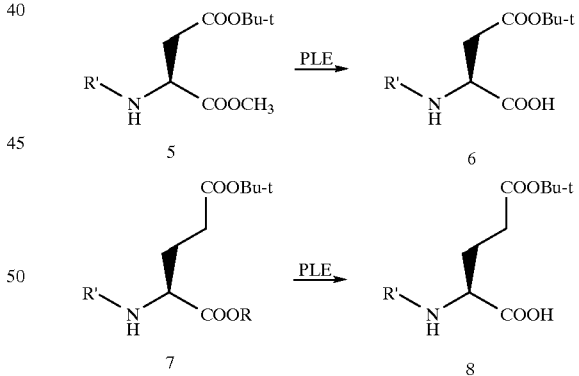

wherein R and R' are defined in Table 1.

Scheme 3. PLE catalyzed hydrolysis of mixed diesters of aspartic acid (Compound 5) and glutamic acid (Compound 7).

A summary of the regioselective α-ester hydrolysis reactions of a number of diester aspartates and diester glutamates with PLE is provided in Table 1. The following abbreviations are used in the columns of Table 1: Sub=substrate, Conc.=concentration of the substrate, % Yld.=percentage yield of product, and MP° C.=melting point in degrees centigrade, dec=decomposition, and lit.MP=literature melting point in degrees centigrade.

TABLE 1

Summary of the regioselective hydrolysis of diester aspartates and diester glutamates with PLE (Ref. 17).

| Sub | R | R' | Conc. (mmol) | Enzyme (Units) | % Yld. | Time hrs | MP ° C. (lit. MP) (reference) |
|---|---|---|---|---|---|---|---|
| 1 | $CH_3$ | H | 5.11 | 300 | 38 | 18.1 | 193–195 dec (195–196) (Ref. 4) |
| 1 | $CH_3$ | $C_6H_5CH_2OCO$ | 4.98 | 300 | 34 | 28.4 | 96–97 (96–98) (Ref. 13) |
| 1 | $CH_3$ | $C_6H_5CH_2OCO$ | 2.63 | 300 | 75 | 30.4 | 96–98 (96–98) (Ref. 13) |
| 1 | $CH_3$ | $CH_3CH_2$ | 2.52 | 300 | 57 | 43.1 | 203–205 (205–207) (Ref.16) |
| 1 | $CH_3$ | $C_6H_5CH_2CO$ | 2.57 | 300 | 62 | 46.8 | 77–78 (Ref. 17) |
| 1 | $CH_3$ | $C_6H_5CH_2CO$ | 1.79 | 150 | 48 | 14.8 | 77–78 (Ref. 17) |
| 1 | $CH_3$ | $CH_3CO$ | 2.50 | 300 | 25 | 24.9 | 143–145 (144–145) (Ref. 14) |
| 1 | $CH_3CH_2$ | H | 4.99 | 300 | 72 | 13.5 | 204–206 (205–206) (Ref. 15) |
| 1 | $(CH_3)_3C$ | H | 0.65 | 150 | 84 | 26.5 | 194–195 dec (198–199) (Ref. 12) |
| 1 | $C_6H_5CH_2$ | H | 2.53 | 150 | 50 | 16.5 | 203–205 dec (205–207) (Ref. 4) |
| 1 | $C_6H_5CH_2$ | $C_6H_5CH_2OCO$ | 0.66* | 450 | 34 | 48.7 | 84–86 (85–86) (Ref. 3b) |
| 3 | $CH_3$ | H | 5.02 | 150 | 60 | 1.5 | 179–181 (180–182) (Ref. 8a) |
| 3 | $CH_3$ | H | 26.00 | 575 | 81 | 4.5 | 179–181 (180–182) (Ref. 8a) |
| 3 | $CH_3CH_2$ | H | 4.96 | 300 | 76 | 17.7 | 195–197 (195–198) (Ref. 8a) |
| 3 | $(CH_3)_3C$ | H | 0.66 | 150 | 50 | 38.1 | 189–190 dec (190–191) (Ref. 12) |
| 3 | $CH_3$ | $CH_3CH_2CO$ | 1.76 | 300 | 90 | 11.1 | oil |
| 5 | — | H | 4.97 | 450 | 50 | 4.5 | 193–195 dec (198–199) (Ref. 12) |
| 5 | — | $(CH_3)_3COCO$ | 4.97 | 450 | 10 | 24.3 | oil |
| 7 | $CH_3$ | H | 4.99 | 300 | 55 | 9.3 | 189–190 (190–191) (Ref.12) |

(*With 5% methanol as a co-solvent)

This invention will be better understood from the Examples which follow. However, one skilled in the art will readily appreciate that the specific methods and results discussed are merely illustrative of the invention and no limitation of the invention is implied.

The unprotected dialkyl amino acid esters are commercially available from Sigma Chemical Company, St. Louis, Mo. The N-acyl and N-alkyl dialkyl amino exters are prepared according to the literature procedures (Refs. 18, 19 and 20).

EXAMPLE 1

General Procedure for preparation of N-protected amino acid monoesters.

In a typical experiment, PLE (150-450 units, suspension in ammonium sulfate; SIGMA® Chemical Company, St. Louis, Mo.) was added to a suspension or solution of N-protected amino acid diester (0.66–13 mmol) in 15 mL of 0.01 M phosphate buffer (pH 7) at room temperature. The pH value was kept at about 7 by the addition of 1N sodium hydroxide. After consumption of 1 mole equivalent of base, the pH was adjusted to 9, then the aqueous phase was washed with chloroform (2×10 mL). The aqueous phase was acidified to pH 2 with 1 N hydrochloric acid, and extracted with chloroform (2×15 mL). The organic phase was washed with water, dried over anhydrous magnesium sulfate, and evaporated under reduced pressure to yield the product (Table 1).

EXAMPLE 2

General Procedure for preparation of unprotected amino acid monoesters.

PLE (150–450 units, suspension in ammonium sulfate; SIGMA® Chemical Company, St. Louis, Mo.) was added to a solution of unprotected amino acid diester (0.66–26 mmol) in 15 mL of 0.01 M phosphate buffer (pH 7) at room temperature. The pH value was kept at about 7 by the addition of 1N sodium hydroxide. After consumption of 1 mole equivalent of base, the pH was adjusted to 3–5 by the addition of concentrated hydrochloric acid, the mixture was diluted with 500 mL of alcohol (methanol, ethanol or 2-propanol) and the precipitated solid was filtered. The crude compound was crystallized from aqueous alcohols to give pure amino acid monoester (Table 1).

References

1. Ohno, M. and Otsuka, M., *Organic Reactions*, 1989, Vol. 37; p.1.
2. (a) Hultin, P. G. et al., *J. Org. Chem.*, 1991, 56, 5375; (b) Toone, E. J. and Jones, J. B., *Tetrahedron: Asymmetry*, 1991, 2, 207; (c) Kobayashi, S. et al., *J. Org. Chem.*, 1990, 55, 1169; (d) Metz, P., *Tetrahedron*, 1989, 45, 7311; (e) Van der Eycken, J., et al., *J. Chem. Soc., Chem. Commun.*, 1989, 306; (f) Sabbioni, G. et al., *J. Org. Chem.*, 1987, 52, 4565; (g) Sabbioni, G. et al., *J. Chem. Soc., Chem. Commun.*, 1984, 236; (h) Adachi, K. et al., *Chima*, 1986, 40, 311.
3. (a) Ineyama, T. et al., The 54th Annual Meeting, Chemical Society of Japan, 1987; (b) Jongejan, J. A. and Duine, J. A., *Tetrahedron Lett.*, 1987, 28, 2767; (c) Hazato, A. et al., *Nippon Kagaku Kaishi* 1983, 9, 1390; (d) *Chem. Abstr.*, 1984, 100, 120720q.
4. Stein, K. A. and Toogood, P. L., *J. Org. Chem.*, 1995, 60, 8110.
5. Swann, Jr., S. et al., *Org. Syntheses Coll. Vol. II*, 1943, 276 and references cited therein.
6. March, J., *Advanced Organic Chemistry*, Third Ed. 1985, 347.
7. Durham, L. J. et al., *J. Org. Syntheses Coll. Vol. IV*, 1963, 635.
8. (a) Albert, R. et al., *Synthesis*, 1987, 635; (b) Saito, Y. and Nagoya, T., *Jpn. Pat.* 77,128,321 1977; (Chem. Abstr., 1977, 88, 105783c).
9. Prestidge, R. L. et al., *J. Org. Chem.*, 1975, 40, 3287.
10. Guibe-Jampel, E. et al., *J. Chem. Soc., Chem. Commun.*, 1987, 1080.
11. (a) Miyazawa, T et al., *J. Chem. Soc., Chem. Commun.*, 1988, 1214; (b) Cohen, S. G. et al., *Biochemistry*, 1963, 2, 820; (c) Cohen, S. G. and Crossley, J., *J. Am. Chem. Soc.* 1964, 86, 4999; (d) Chen, S. T. and Wang, K.-T.,

*Synthesis,* 1987, 581; (e) Pugniere, M. et al., *Tetrahedron: Asymmetry,* 1992, 3, 1015.
12. Roeske, R., *J. Org. Chem.,* 1963, 28, 1251.
13. Oki, K.; Suzuki, K.; Tuchida, S.; Saito, T.; and Kotake, H., *Bull. Chem. Soc. Jpn.,* 1970, 43, 2554.
14. Marchatti, E.; Mattalia, G.; Curatolo, F.; and Bergesi, G., *Ann. Chim.,* 1967, 57, 624.
15. Wiecozorek, W.; Bukowska-Strzyzewska, M.; Olma, A.; Kaminski, Z. J.; and Leplawy, M. T., *J. Crystallogr. Spectrosc. Res.,* 1991, 21, 107.
16. Liu, K.-C. and Wang, D., *Arch. Pharmaz.,* 1975, 308, 564.
17. Characterization of all of the compounds was confirmed by melting point (mp), infra red spectroscopy (IR), and nuclear magnetic resonance spectroscopy (NMR).
18. Bodanszky, M., "Principals of Peptide Synthesis" (Springer-Verlag), 1984, 85.
19. Bodanszky, M. and Bodanszky, A., "The Practice of Peptide Synthesis" (Springer-Verlag), 1984.
20. Ohfune, Y.; Kurokawa, N.; Higuchi, N.; Saito, M.; Hashimoto, M.; and Tanaka, T., *Chemistry Letters,* 1984, 441.

What is claimed:

1. A method for the preparation of an N-protected β-ester aspartate which comprises:

reacting an N-protected diester aspartate comprising an α-ester group and a β-ester group with an amount of a pig liver esterase enzyme effective to hydrolyze selectively the α-ester group and form the N-protected β-ester aspartate.

2. The method of claim 1, wherein the α-ester group and the β-ester group may be the same or different.

3. The method of claim 2, wherein each of the α-ester group and the β-ester group is an alkyl ester.

4. The method of claim 3, wherein the α-ester group and the β-ester group are independently selected from the group consisting of $CH_3OCO-$, $C_2H_5OCO-$, $(CH_3)_3COCO-$ and $C_6H_5CH_2OCO-$.

5. The method of claim 1, wherein the N-protecting group is an alkyl or alkyl carbonyl.

6. The method of claim 5, wherein the N-protecting group is selected from the group consisting of $CH_3CH_2-$, $CH_3CO-$, $C_6H_5CH_2CO-$, $C_6H_5CH_2OCO-$, $CH_3CH_2CO-$ and $(CH_3)_3CCO-$.

7. The method of claim 1, further comprising the presence of a suitable buffer.

8. The method of claim 7, wherein the buffer is selected from the group consisting of phosphate, imidazole, piperazine-N,N'-bis(2-ethanesulfonic acid), N-2-acetamidoiminodiacetic acid and 3-(N-morpholino)propanesulfonic acid.

9. The method of claim 8, wherein the phosphate buffer is potassium.

10. The method of claim 1, wherein the reaction is carried out at a pH range of about 6 to about 8.

11. The method of claim 10, wherein the reaction is carried out at a pH range of about 6.5 to about 7.5.

12. The method of claim 1, wherein the amount of pig liver esterase enzyme is about 150 units to about 575 units.

13. The method of claim 7, further comprising the presence of a suitable organic solvent.

14. The method of claim 13, wherein the organic solvent is selected from the group consisting of acetone, methanol, ethanol, N,N'-dimethylformamide, and tetrahydrofuran.

* * * * *